United States Patent
Shinozuka et al.

(10) Patent No.: US 6,720,164 B1
(45) Date of Patent: *Apr. 13, 2004

(54) METHOD OF DETERMINING SUBSTRATE, AND BIOSENSOR

(75) Inventors: Naoki Shinozuka, Sapporo (JP); Toru Yokoyama, Sapporo (JP); Kenji Nakamura, Sapporo (JP)

(73) Assignee: Sapporo Immuno Diagnostic Laboratory, Hokkaido (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/914,292

(22) PCT Filed: Mar. 19, 1999

(86) PCT No.: PCT/JP99/01392

§ 371 (c)(1),
(2), (4) Date: Aug. 27, 2001

(87) PCT Pub. No.: WO00/57166

PCT Pub. Date: Sep. 28, 2000

(51) Int. Cl.$^7$ ................................................ C12Q 1/32
(52) U.S. Cl. ........................ 435/26; 435/25; 204/403; 205/777.5
(58) Field of Search ..................... 435/26, 25, 287.1, 435/817, 283.1, 257.1; 204/403; 205/777.5

(56) References Cited

U.S. PATENT DOCUMENTS

| | | | |
|---|---|---|---|
| 4,816,394 A | | 3/1989 | Ushizawa et al. ............. 435/26 |
| 5,298,414 A | | 3/1994 | Bruce et al. ................... 435/26 |
| 5,387,515 A | | 2/1995 | Bruce et al. ................. 435/148 |
| 5,639,672 A | * | 6/1997 | Burd et al. ................... 436/525 |
| 6,130,054 A | * | 10/2000 | Iwata et al. ................... 435/17 |
| 6,468,416 B1 | * | 10/2002 | Nakamura et al. ........ 205/777.5 |

FOREIGN PATENT DOCUMENTS

| | | | |
|---|---|---|---|
| EP | 0 415 124 A2 | 3/1991 | ............. C12M/1/40 |
| EP | 0 908 453 | 4/1999 | ......... C07D/257/04 |
| EksP | 0908453 A1 * | 4/1999 | ......... C07D/257/04 |
| JP | 01 230026 | 9/1989 | ............. G02F/1/17 |
| JP | 9-286784 | 11/1997 | ......... C07D/257/04 |
| JP | 09286784 A * | 11/1997 | ......... C07D/257/04 |
| WO | WO 82.03729 | 10/1982 | ............. H01M/8/16 |
| WO | WO 94/01578 | 1/1994 | ............. C12Q/1/42 |
| WO | WO 97/14965 | 4/1997 | ......... G01N/33/553 |

OTHER PUBLICATIONS

Analytical Chem. 59,2111–2115(1987), Relevancy: Development of NADH sensor which uses hexacyanoiron ion as an electron mediater.

Analytica Chemica Acta 329,215–221(1996), Relevancy: Development of alcohol sensor using a Meldola s blue as an electron mediator.

Biosensors & Bioelectronics vol. 11, No. 12, 1267–1275(1996), Relevancy: Development of NADH sensor using a quinone as an electron mediator.

Analytical Chemica Acta 336,57–65(1996), Relevancy: Development of lactate sensor without any electron mediators.

Analytical Chem. 70,4320–4325(1998), Relevancy: Development of lipoamide sensor wherein ferrocene is used as an electron.

Biol. Chem. vol. 379,1207–1211(1998), Relevancy: Development of glucose sensor wherein pyrroloquinoline quinone is used as an electron mediator.

* cited by examiner

Primary Examiner—Ralph Gitomer
(74) Attorney, Agent, or Firm—Nixon & Vanderhye P.C.

(57) ABSTRACT

A method of quantifying a substrate, by which the substrate contained in various samples can be conveniently and quickly quantified without resort to any troublesome pretreatments, and a biosensor. More particularly speaking, a method of quantifying a substrate in a sample by using an electrode system made of electrically conductive materials and a reaction reagent comprising at least a dehydrogenase, a coenzyme an electron mediator and a tetrazolium salt, which comprises performing an enzyme reaction and a redox reaction between the reaction reagent and the substrate in the sample, and detecting a formazan formed as the final reaction product by using the electrode system and a if biosensor with the use of the same are provided.

6 Claims, 6 Drawing Sheets

1: Insulating support
2: Working electrode
3: Counter electrode
4: Insulating layer
5: Absorbent carrier Tetrazolium salt    Formazan R₁, R₂, R₃ : alkyl group
X⁻ : halogen

METHOD OF DETERMINING SUBSTRATE, AND BIOSENSOR

This application was filed under 371 of International Application No. PCT/JP99/01392 filed Mar. 19, 1999.

FIELD OF THE INVENTION

This invention relates to a method of conveniently and quickly quantifying substrates contained in various samples, for example, biological samples such as blood, urine, saliva and sweat, foods and environmental samples and a biosensor. More particularly, it relates to a method of quantifying a substrate through reactions by using an electrode system made of electrically conductive materials and various reagents and a biosensor with the use of the same.

BACKGROUND OF THE INVENTION

It has been considered that methods of quantifying substrates by using dehydrogenases and coenzymes are useful in the field of analytical chemistry for clinical examinations, food analysis, etc. An enzyme reaction with the use of a dehydrogenase and a coenzyme as catalysts means a reaction whereby a substrate contained in a sample is specifically oxidized and, at the same time, the coenzyme is reduced. There have been confirmed several hundred dehydrogenase reactions occurring in vivo. These enzyme reactions are highly important because they are applicable to the quantification of substrates in samples, the measurement of enzyme activities, etc. In these measurement methods, reduced coenzymes formed by the reactions are detected.

These reduced coenzymes formed as the reaction products are quantified by liquid chromatography (Analytical Biochemistry, Vol.146, p.118 (1985)), UV absorption spectroscopy (Clinical Chemistry, Vol.22, p.151 (1976)) and the like. Use is also made of a method which comprises subjecting a reduced coenzyme to a redox reaction with an oxidant selected from among tetrazolium salts (Japanese Patent Public Disclosure No.286784/97, Analyst, Vol. 120, p.113(1995)), ferricyanides, quinones, cytochromes, metal ions, etc. and then quantifying the reduced product thus formed by the absorption spectroscopy in the visible region. However, none of these methods enables convenient and quick measurement, since it is needed therein to perform pretreatments such as dilution or separation. Another problem is that large-scale and expensive measurement apparatuses are needed when employing these methods.

In recent years, there have been employed biosensors of electrochemical detection type as means of conveniently and quickly quantifying reduced coenzymes formed by enzyme reactions. In these cases, it is anticipated that reduced coenzymes would be directly detected electrochemically (Analyica Chimica Acta, Vol.336, p.57 (1996)). However, reduced coenzymes can hardly undergo redox reactions via electron transfer. Therefore, it is necessary to apply a high potential to directly oxidize a reduced coenzyme on electrodes. However, the application of such a high potential causes pollution and damage of the electrodes or induces effects of coexisting matters. Attempts to solve these problems have been made by using electron mediators as can be seen from a number of reports and patents concerning biosensors published so far (Japanese Patent Public Disclosure No.165199/98). Examples of electron mediators employed in biosensors at present include phenazine derivatives such as 1-methoxy-5-methylphenazinium methylsulfate (1-methoxy PMS) (Analyst, Vol.119, p.253 (1994)), Meldola's Blue (Analytica Chimica Acta, Vol.329, p.215 (1996)), ferricyanides (Analytical Chemistry, Vol.59, p.2111 (1987)), ferrocene (Analytical Chemistry, Vol.70, p.4320 (1998)) and quinones (Bioscience & Bioelectronics, Vol.11, p.1267 (1996)). Such an electron mediator is reduced by a redox reaction with a reduced enzyme and the reduced electron mediator thus formed easily undergoes a redox reaction by applying a potential on electrodes. Therefore, detection can be made by applying a lower potential, compared with the case of oxidizing a reduced coenzyme directly on electrodes.

The present inventors have devised biosensors of an integrated type consisting of a reaction reagent, which comprises various dehydrogenases, oxidized nicotinamide adenine dinucleotide ($NAD^+$) as a coenzyme and an electron mediator 1-methoxy PMS, with an electrode system (Japanese Patent Application No.201553/98; PCT/JP98/03194) and constructed biosensors whereby various substrates can be conveniently and quickly quantified. In these biosensors, an absorbent carrier carrying all of the reaction reagents is located between a working electrode and a counter electrode which are made of electrically conductive materials and formed by the printing method. It is confirmed that a highly favorable linear response current depending on the concentration of each substrate can be obtained thereby. However, subsequent studies have revealed that these biosensors still suffer from the problem. Namely, the response current in the low substrate concentration region is liable to be affected by coexisting matters. This is seemingly because electron mediators are chemically unstable due to the very low standard redox potential thereof and, therefore, liable to undergo redox reactions with redox matters coexisting in samples, which results in fluctuation and decrease in the response current in the low substrate concentration region. To conduct highly accurate quantification with a stable response current, it is therefore necessary to further improve the system.

SUMMARY OF THE INVENTION

To solve the above-described problems, the present invention provides a method of quantifying a substrate by using an electrode system made of electrically conductive materials and a reaction reagent comprising at least a dehydrogenase, a coenzyme, an electron mediator and a tetrazolium salt and a biosensor.

Compared with the conventional methods with the direct oxidization of reduced coenzymes or the use of various electron mediators. the method according to the present invention makes it possible to reduce the fluctuation in the response current since a chemically stable formazan is formed as the final product. In the method of the present invention, moreover, the response current is largely increased and the detection sensitivity is elevated. which makes it possible to quantify a substrate in the lower concentration region. Consequently, a substrate in a sample can be quantified with high accuracy.

DESCRIPTION OF THE INVENTION

The present invention provides a method of quantifying a substrate by using an electrode system consisting of at least a working electrode and a counter electrode made of electrically conductive materials and a reaction reagent comprising at least a dehydrogenase, a coenzyme, an electron mediator and a tetrazolium salt, and a biosensor in which the reaction reagent and the electrode system are integrated and which enables convenient and quick quantification.

In the present invention, the substrate in the sample undergoes a specific enzyme reaction under the action of the dehydrogenase and the coenzyme contained in the reaction reagent to form a reduced coenzyme. Then a redox reaction quickly proceeds between this reduced coenzyme and the electron mediator and the tetrazolium salt, and a chemically stable formazan is formed as the final product. As the above mentioned series of reactions proceed, formazan is produced depending on the concentration of the substrate. Next, the formazan is electrochemically changed by applying a potential to the electrode system and the thus arising response current is detected. Since this response current occurring from the formazan depends on the substrate concentration, the substrate can be thus quantified. FIG. 5 roughly shows the process of a series of reactions as described above. FIG. 6 shows the fundamental structural formulae of the tetrazolium salt and the formazan formed as the final product.

The substrate which can be quantified in the present invention involves any substrates in dehydrogenation reactions whereby reduced coenzymes are formed by using dehydrogenases as a catalyst. Use of such an enzyme reaction makes it possible not only to quantify a substrate but also to measure enzyme activity, etc. Namely, substrates over an extremely large range are usable in the method according to the present invention, which makes it applicable to various measurements. Particular examples of the substrate include alcohols, galactose, glucose, cholesterol, lactic acid, phenylalanine and leucine. However, it is obvious that other various substrates can be quantified by the method of the present invention.

Since a chemically stable formazan is formed as the final product in the method of the present invention, a reduction in the fluctuation response current can be obtained. It has been already confirmed by the above-described spectroscopy method that the reaction of forming a formazan from a substrate smoothly and quantitatively proceeds (Japanese Patent Public Disclosure No.286784/97, Analyst, Vol.120, p.113 (1995)). According to the present invention, it has been further clarified that detection can be carried out by using an electrode system and thus a more useful quantification method has been established. As a result, a current density of about 120 $\mu A/cm^2$ is established by the biosensor of the present invention and thus the response current is largely increased and the detection sensitivity is improved, since the current density of the conventional biosensors constructed ranges from about 4 to 12 $\mu A/cm^2$ per mM of a substrate and the current densities of the existing biosensors with the use, as the electron mediator, of ferricyanides (Analytical Chemistry, Vol. 59, p.2111 (1987), ferrocene (Analytical Chemistry, Vol.70, p.4320 (1998)) and quinones (Bioscience & Bioelectronics, Vol.11, p.1267 (1996)) are respectively about 2 $\mu A/cm^2$ (calculated from FIG. 6, p.2114), about 6 $\mu A/cm^2$ (calculated from FIG. 4, p.4323) and about 10 $\mu A/cm^2$ (FIG. 10, p.1273). Moreover, the present invention enables quantification of a substrate in a lower concentration region. Thus, a substrate can be quantified at a high accuracy by using the quantification method and biosensor according to the present invention.

Figure 1:
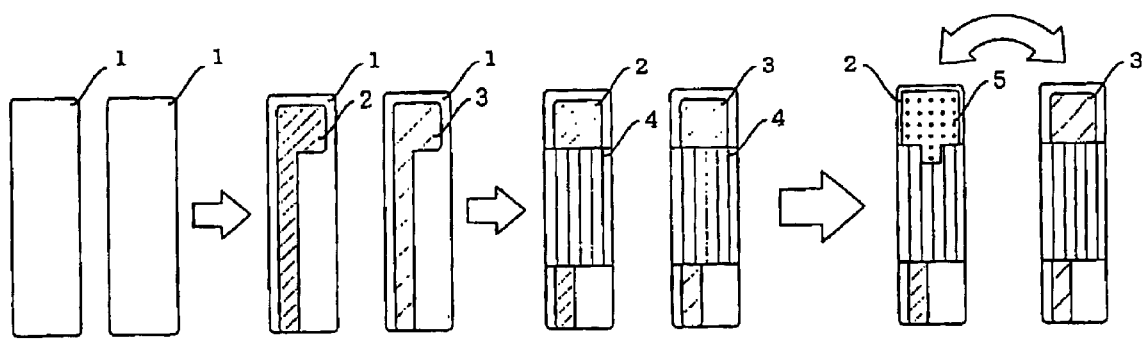
FIG. 1 is a diagram schematically showing the constitution of the biosensor in an example of the present invention.
Figure 1:
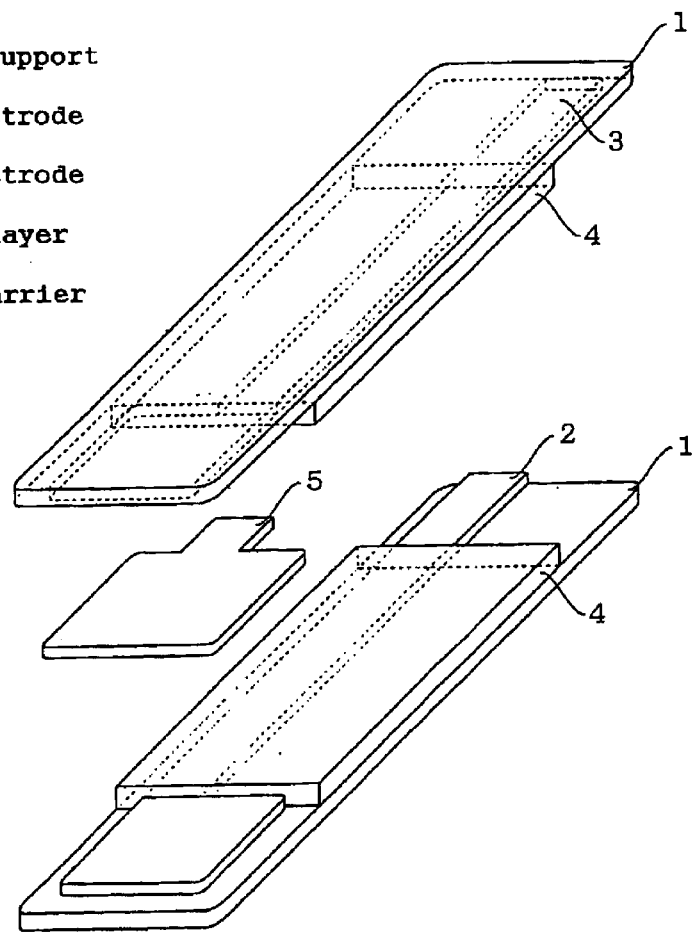

The symbols given in the above figures have the following meanings: 1 stands for an insulating support; 2 stands for a working electrode; 3 stands for a counter electrode; 4 stands for an insulating layer: and 5 stands for an absorbent carrier.

DESCRIPTION OF THE PREFERRED EMBODIMENTS

The electrode system to be used in the present invention may be an arbitrary one without restriction, so long as it is made of electrically conductive materials and is electrochemically stable. Examples of materials usable therefor include carbon, gold, silver, silver/silver chloride (Ag/AgCl), nickel, platinum, platinum black, palladium and alloys of these metals. As the results of examinations on various materials, it has been found out that carbon materials are favorable as the working electrode in the electrode system of the present invention, since they are less expensive and chemically stable.

The term "carbon materials" as used herein means materials containing carbon. Any carbon materials employed in the conventional carbon electrodes are usable herein without any particular restriction. For example, use can be made of carbon fiber, carbon black, carbon paste, glassy carbon, graphite and the like.

By using such a carbon material, an electrode is formed on the insulating support by a method commonly employed. Usually, the carbon material is made into a paste by using a resin binder, etc., screen-printed and then dried by heating to thereby form the electrode.

The insulating support may be made of glass, glass epoxy, ceramics, plastics, etc., though the material thereof is not restricted thereto so long as it is not damaged in the step of forming the electrodes by printing or adding a sample. For example, it is possible to use plastic films made of polyester, polyethylene, polyethylene terephthalate, poylystyrene, polypropylene, etc. It is found out that polyester films are favorable herein, since they are less expensive and excellent in adhesiveness to conductive inks and processing properties.

The printing method is not restricted to the screen-printing but use may be made of, for example, gravure printing, offset printing or ink jet printing.

The substrate which can be quantified by the method of the present invention is not particularly restricted, so long as it can form a reduced coenzyme with the use of a dehydrogenase as a catalyst. Namely, any substrate can be quantified. For example, use can be made of alanine, alcohols, aldehydes, isocitric acid, uridine-5'-diphosphoglucose, galactose, formic acid, glycerylaldehyde-3-phosphate, glycerol, glycerol-3-phosphate, glucose, glucose-6-phosphate, glutamic acid, cholesterol, sarcosine, sorbitol, carbonic acid, lactic acid, 3-hydroxybutyric acid, pyruvic acid, phenylalanine, fructose, 6-phosphogluconic acid, formaldehyde, mannitol, malic acid, leucine, etc.

The dehydrogenase to be used in the present invention is not particularly restricted, so long as it is an enzyme capable of forming a reduced coenzyme. The origin of the dehydrogenase is not restricted either. For example, use can be made of alanine dehydrogenase, alcohol dehydrogenase, aldehyde dehydrogenase, isocitrate dehydrogenase, uridine-5'-diphospho-glucose dehydrogenase, galactose dehydrogenase, formate dehydrogenase, glycerylaldehyde-3-phosphate dehydrogenase, glycerol dehydrogenase, glycerol-3-phosphate dehydrogenase, glucose dehydrogenase, glucose-6-phosphate dehydrogenase, glutamate dehydrogenase, cholesterol dehydrogenase, sarcosine dehydrogenase, sorbitol dehydrogenase, carbonate dehydrogenase, lactate dehydrogenase, 3-hydroxybutyrate dehydrogenase, pyruvate dehydrogenase, phenylalanine dehydrogenase, fructose dehydrogenase, 6-phosphogluconate dehydrogenase, formaldehyde dehydrogenase, mannitol dehydrogenase, malate dehydrogenase, leucine dehydrogenase, etc.

The electron mediator is not particularly restricted, so long as it can quickly undergo a redox reaction with a reduced coenzyme and a tetrazolium salt. For example, use can be made of quinones, diaphorase, cytochromes, biologen. phenazines, phenoxazines, phenothiazines, ferricyanides, ferredoxins, ferrocene and derivatives thereof, etc. Among all, phenazines show a high response stability. In particular, it has been found out that 1-methoxy PMS is preferable as the electron mediator in the present invention because of its improved storage stability and reactivity with reduced coenzymes and tetrazolium salts.

The tetrazolium salt is not particularly restricted, so long as it can form formazan. Among all, it has been found out that 2-(4-iodophenyl)-3-(4-nitrophenyl)-5-(2,4-disulfophenyl)-2H-tetrazolium monosodium salt (WST-1) is preferable as the tetrazolium salt to be used in the present invention, since it provides a water-soluble and chemically stable formazan by reduction and the thus formed formazan shows a specific response in the electrode system.

EXAMPLES

Now, the invention will be illustrated in greater detail by reference to the following examples. However, it is to be understood that the invention is not construed as being restricted thereto.

Example 1

Construction of Biosensor

FIG. 1 is a diagram schematically showing the constitution of the biosensor in an example of the present invention.

On an insulating support 1 made of a polyester film (manufactured by Diafoil Hoechst Co.), a working electrode 2 and a counter electrode 3 were formed by screen-printing respectively using a conductive graphite ink (manufactured by Acheson Japan Ltd.) and a conductive Ag/AgCl ink (manufactured by Acheson Japan Ltd.) followed by drying by heating (60° C., 1 hour), thereby forming an electrode system.

A buffering component, which was employed for regulating the pH value of the enzyme reaction to the optimum level was adsorbed on the working electrode 2 and fixed by drying (40° C., 15 minutes).

1-Methoxy PMS (manufactured by Dojindo Laboratories Co., Ltd.) serving as the electron mediator was adsorbed on the counter electrode 3 and fixed by drying (40° C., 15 minutes).

WST-1 (manufactured by Dojindo Laboratories Co., Ltd.) employed as the tetrazolium salt, a dehydrogenase and a coenzyme were dissolved in a phosphate buffer (pH 8.0, 20 mM), then adsorbed on an absorbent carrier 5 made of cellulose fiber (manufactured by Advantec Toyo) and fixed by drying (40° C., 15 minutes).

The working electrode 2 having the buffer component fixed thereto and the counter electrode 3 having 1-methoxy PMS fixed thereto were faced to each other and the absorbent carrier containing WST-1, the dehydrogenase and the coenzyme was located between these electrodes of the electrode system, thereby forming a biosensor.

Example 2

Measurement of the Fundamental Response of Biosensor

Figure 2:
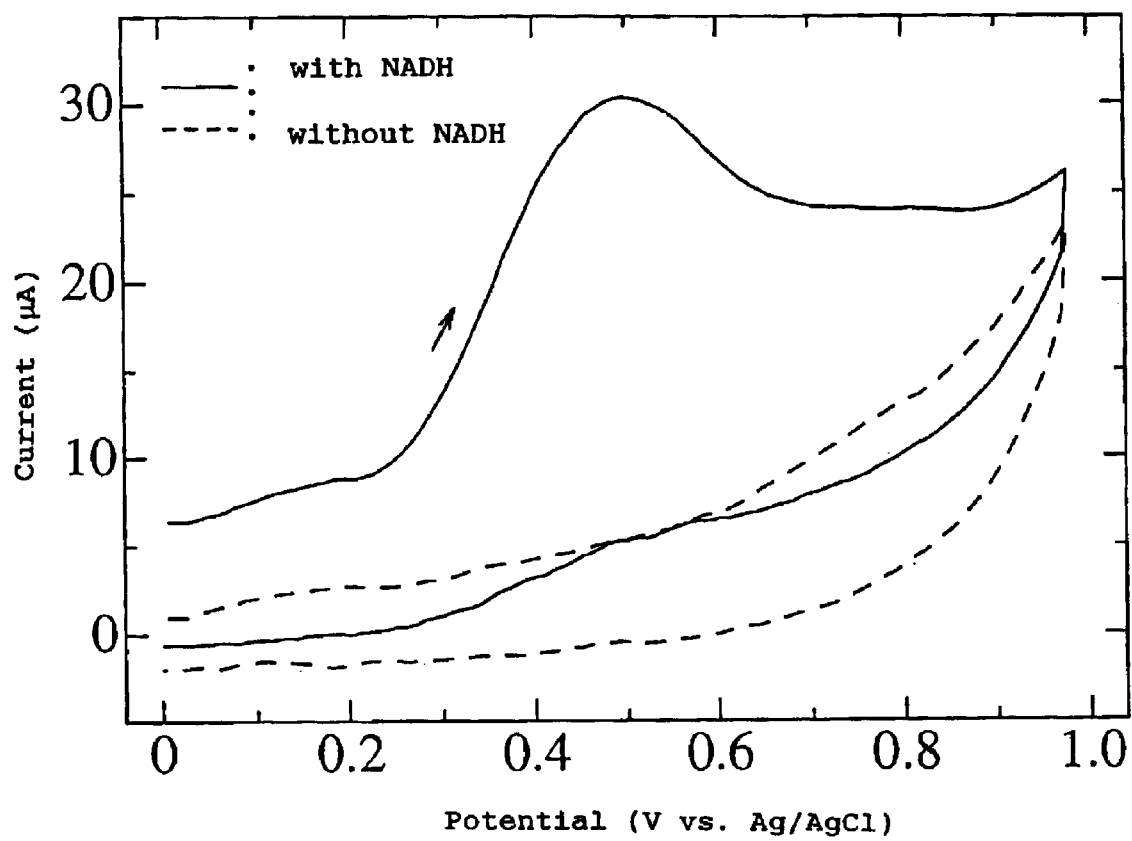
FIG. 2 is a graph showing the fundamental responses of the biosensor in Example 2.

FIG. 2 shows the results of the measurement of the fundamental responses of the biosensor constructed in Example 1.

In this example, 5 µL portions of a standard solution containing NADH and another standard solution free from NADH were added to the above-described sensor. Then a formazan was formed by the redox reaction between the added NADH and 1-methoxy PMS and WST-1. The obtained results show the cyclic voltammogram of the formazan (sweep speed: 50 mV/sec; Model HZ-3000 manufactured by Hokuto Denko Corporation). The solid line shows the result obtained by using the standard solution containing NADH (1.5 mM) while the broken line shows the result obtained by using the NADH-free standard solution.

As these results show, an oxidation peak appeared at around +500 mV vs. Ag/AgCl and thus a response current characteristic to formazan could be obtained.

Example 3

Quantification of NADH

Figure 3:
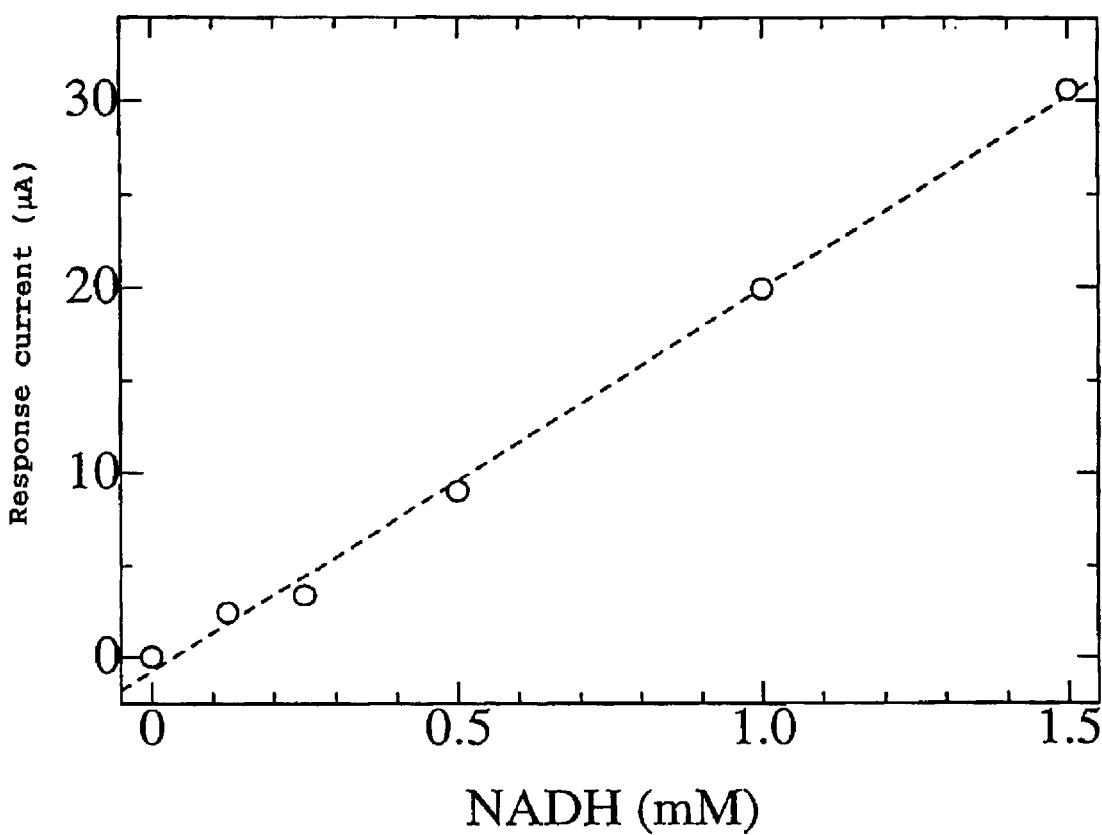
FIG. 3 is a graph showing the result of the response to reduced nicotinamide adenine dinucleotide (NADH) in Example 3.

FIG. 3 shows the result of the measurement of NADH, which is a reduced coenzyme formed by reacting a sample with a dehydrogenase and a coenzyme, by using the biosensor constructed in Example 1.

Sixty seconds after adding 5 µL of a sample containing NADH, a potential was applied at +700 mV vs. Ag/AgCl (Model HZ-3000 manufactured by Hokuto Denko Corporation) by using the counter electrode as the standard and the response current was measured (Model HZ-3000 manufactured by Hokuto Denko Corporation).

As a result, a response of a very good linearity was achieved in an NADH concentration range of from 0 to 1.5 mM.

Thus, it is expected that the quantification method and biosensor according to the present invention are applicable to enzyme reactions with the use of any dehydrogenases and coenzymes forming reduced coenzymes.

Example 4

Quantification of L-phenylalanine

Figure 4:
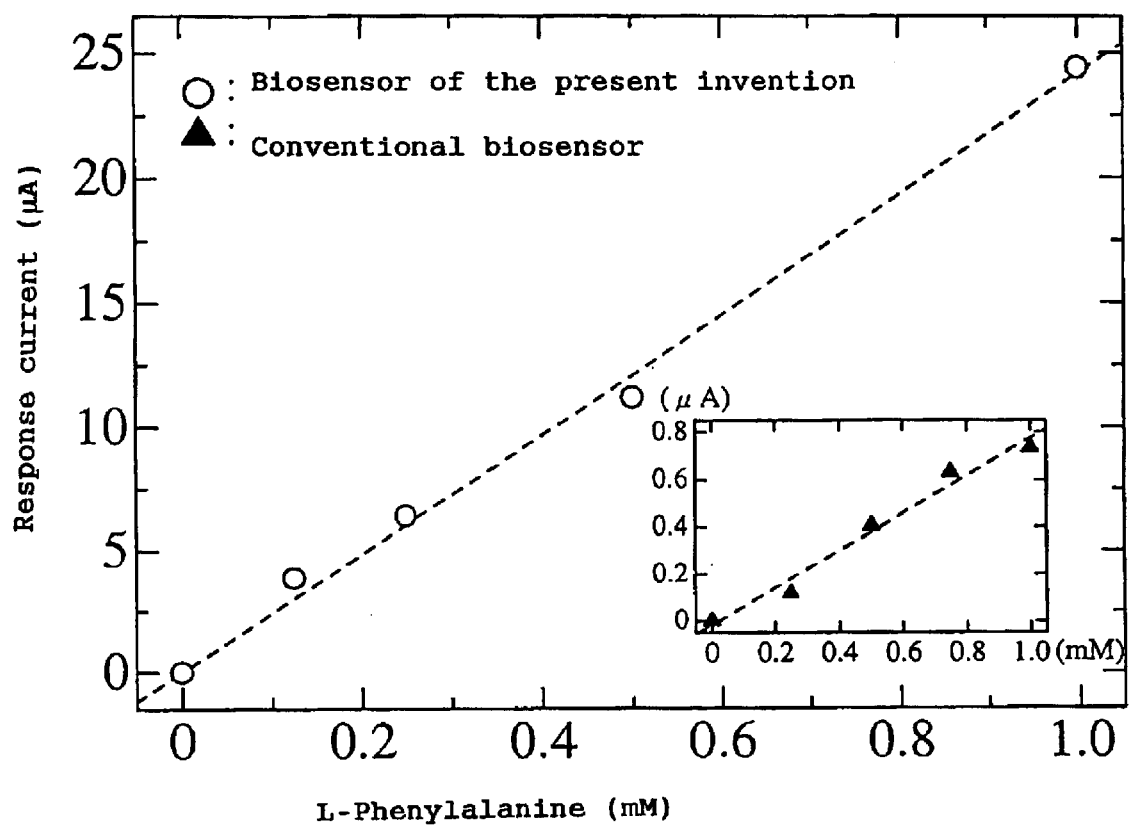
FIG. 4 is a graph showing the results of the response to L-phenylalanine in Example 4.

FIG. 4 shows the result of the measurement of a standard solution containing L-phenylalanine with the use of the biosensor constructed in Example 1 by reference to Example 3.

In this example, 5 µL of a standard solution containing L-phenylalanine was added to a biosensor constructed with the use of L-phenylalanine dehydrogenase (EC 1.4.1.20, manufactured by Unitika Ltd.). After 60 seconds, a potential was applied at +700 mV vs. Ag/AgCl by using the counter electrode as the standard and the response current was measured.

FIG. 4 also shows the result of the measurement with the use of a conventional biosensor for comparison.

In the case of the conventional biosensor, 5 µL of a standard solution containing L-phenylalanine was added and, after 60 seconds, a potential was applied at −220 mV vs. Ag/AgCl by using the counter electrode as the standard and the response current was measured.

Figure 5:
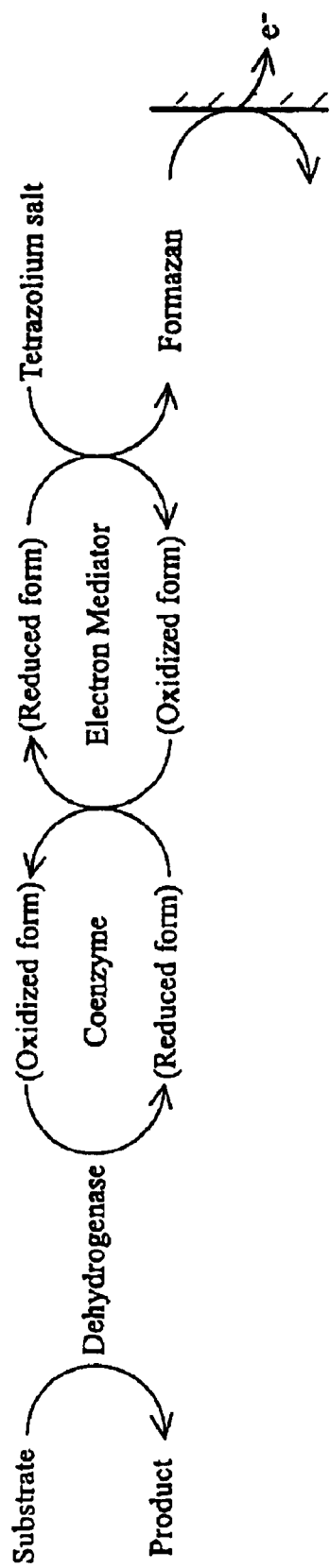
FIG. 5 is a reaction model view of the present invention.
Figure 6:
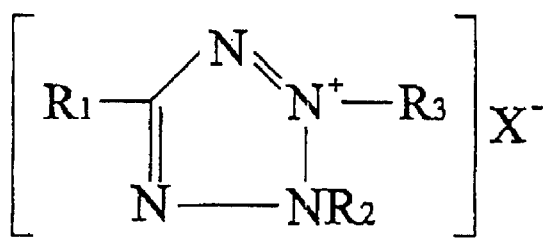
FIG. 6 shows the structural formulae of tetrazolium salts and formazans.
Figure 6:
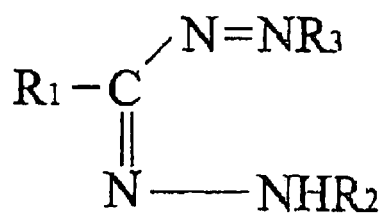

When a sample is added to the reaction reagent, the substrate in the sample undergoes a specific enzyme reaction under the action of the dehydrogenase and the coenzyme contained in the reaction reagent to thereby form the reduced coenzyme. Then a redox reaction quickly proceeds between this reduced coenzyme and the electron mediator and the tetrazolium salt and a chemically stable formazan is formed as the final product. Subsequently, a potential is applied to the electrode system and thus the formazan is electrochemically changed. Then the response current thus arising is detected. Since this response current depends on the substrate concentration. the substrate can be quantified thereby. FIG. 5 shows a reaction model view of the present invention as described above. FIG. 6 shows the fundamental structural formulae of tetrazolium salts and formazans.

As a result, a response of a very good linearity was achieved in an L-phenylalanine concentration range of from 0 to 1 mM. A very large response current showing a current density of about 120 $\mu A/cm^2$ per mM of L-phenylalanine was obtained.

Although use was made of a biosensor involving a two-electrode system having a working electrode and a counter electrode in the above examples, quantification with a higher accuracy can be also made by using a three-electrode system with a reference electrode.

What is claimed is:

1. A method of quantifying a substrate in a sample which method comprises the steps of:
    (a) contacting a sample containing a substrate with a reaction reagent comprising at least a dehydrogenase, a coenzyme, an electron mediator and a (2-(4-indophenyl)-3-(4-nitrophenyl)-5-(2,4-disulfophenyl)-2-tetrazolium performing an enzyme reaction and a redox reaction between which produces a water-soluble, stable formazan, then,
    (b) detecting the water-soluble formazan formed from the (2-(4-indophenyl)-3-(4-nitrophenyl)-5-(2,4-disulfophenyl)-2H-tetrazolium as the final reaction product using an electrode system made of electrically conductive materials, and
    (c) correlating an increase in electrical current in the electrode system with a quantity of substrate in the sample.

2. The method as claimed in claim 1 wherein said substrate is alanine, an alcohol, an aldehyde, isocitric acid, uridine-5'-diphospho-glucose, galactose, formic acid, glycerylaldehyde-3-phosphate, glycerol, glycerol-3-phosphate, glucose, glucose-6-phosphate, glutamaic acid, cholesterol, sarcosine, sorbitol, carbonic acid, lactic acid, 3-hydroxybutyric acid, pyruvic acid, phenylalanine, fructose, 6-phosphogluconic acid, formaldehyde, mannitol, malic acid or leucine.

3. The method as claimed in claim 1 wherein said formazan is electrochemically changed by applying a certain potential to said electrode system and the thus arising response current is detected.

4. A biosensor for detecting said formazan by using the method as claimed in claim 1 wherein said reaction reagent and electrode system consisting of at least a working electrode and a counter electrode made of electrically conductive materials are integrated.

5. The biosensor as claimed in claim 4 wherein said formazan is electrochemically changed by applying a certain potential to said electrode system and the thus arising response current is detected.

6. The biosensor of claim 4 or 5 wherein the following three components (a), (b) and (c) are individually immobilized:
    (a) said (2-(4-indophenyl)-3-(4-nitrophenyl)-5-(2,4-disulfophenyl)-2-tetrazolium, a dehydrogenase and a coenzyme immobilized on an absorbent carrier;
    (b) an electron mediator immobilized on the counter electrode; and
    (c) components of a buffer immobilized on the working electrode.

* * * * *